United States Patent
Perszyk et al.

(10) Patent No.: US 10,441,421 B2
(45) Date of Patent: Oct. 15, 2019

(54) PROSTHETIC MITRAL VALVE

(71) Applicant: St. Jude Medical, Cardiology Division, Inc., St. Paul, MN (US)

(72) Inventors: Brian Joseph Perszyk, Shoreview, MN (US); Mathias Charles Glimsdale, St. Michael, MN (US); Kristopher Henry Vietmeier, Monticello, MN (US); Theodore Paul Dale, Corcoran, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 62 days.

(21) Appl. No.: 15/796,184

(22) Filed: Oct. 27, 2017

(65) Prior Publication Data

US 2018/0116798 A1 May 3, 2018

Related U.S. Application Data

(60) Provisional application No. 62/457,374, filed on Feb. 10, 2017, provisional application No. 62/414,125, filed on Oct. 28, 2016.

(51) Int. Cl.
- *A61F 2/24* (2006.01)
- *A61F 2/848* (2013.01)
- *A61F 2/00* (2006.01)

(52) U.S. Cl.
CPC .......... *A61F 2/2454* (2013.01); *A61F 2/2418* (2013.01); *A61F 2/2445* (2013.01);
(Continued)

(58) Field of Classification Search
CPC ...... A61F 2/2418; A61F 2/848; A61F 2/0077; A61F 2/2409; A61F 2002/8483;
(Continued)

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| DE | 19857887 A1 | 7/2000 |
| DE | 10121210 B4 | 11/2005 |

(Continued)

OTHER PUBLICATIONS

"Direct-Access Valve Replacement", Christoph H. Huber, et al., Journal of the American College of Cardiology, vol. 46, No. 2, (Jul. 19, 2005).

(Continued)

*Primary Examiner* — Paul B Prebilic
(74) *Attorney, Agent, or Firm* — Lerner, David, Littenberg, Krumholz & Mentlik, LLP

(57) ABSTRACT

A prosthetic heart valve having an inflow end and an outflow end includes a stent having a collapsed condition, an expanded condition, and cells arranged in circumferential rows. The stent has an anterior side configured to be disposed adjacent an anterior native valve leaflet and a posterior side configured to be disposed adjacent a posterior native valve leaflet. A valve assembly having a plurality of leaflets is disposed within the stent and a flange is disposed about the stent. The flange includes a flared portion adjacent the inflow end and a body portion extending from the flared portion to the outflow end, the flange extending between a first set of attachment points adjacent the inflow end, and a second set of attachment points adjacent the outflow end.

19 Claims, 15 Drawing Sheets

(52) U.S. Cl.
CPC ............ *A61F 2/848* (2013.01); *A61F 2/0077* (2013.01); *A61F 2/2409* (2013.01); *A61F 2/2427* (2013.01); *A61F 2002/8483* (2013.01); *A61F 2210/0076* (2013.01); *A61F 2220/005* (2013.01); *A61F 2220/0016* (2013.01); *A61F 2220/0058* (2013.01); *A61F 2220/0075* (2013.01); *A61F 2230/0006* (2013.01); *A61F 2230/0008* (2013.01); *A61F 2230/0013* (2013.01); *A61F 2230/0026* (2013.01); *A61F 2230/0052* (2013.01); *A61F 2250/006* (2013.01); *A61F 2250/0037* (2013.01); *A61F 2250/0039* (2013.01); *A61F 2250/0069* (2013.01)

(58) Field of Classification Search
CPC ...... A61F 2220/0016; A61F 2220/0008; A61F 2230/0065; A61F 2250/0037; A61F 2250/0039; A61F 2250/0026; A61F 2250/006; A61F 2250/0063; A61F 2250/0069
See application file for complete search history.

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,415,664 A | 5/1995 | Pinchuk |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,857,845 B2 | 12/2010 | Stacchino et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| D684,692 S | 6/2013 | Braido |
| 8,454,686 B2 | 6/2013 | Alkhatib |
| 8,500,798 B2 | 8/2013 | Rowe et al. |
| 8,568,474 B2 | 10/2013 | Yeung et al. |

(56) References Cited

U.S. PATENT DOCUMENTS

| | | |
|---|---|---|
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |
| 8,728,154 B2 | 5/2014 | Alkhatib |
| 8,747,459 B2 | 6/2014 | Nguyen et al. |
| 8,764,820 B2 | 7/2014 | Dehdashtian et al. |
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,661 B2 | 9/2014 | Manasse |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0210304 A1 | 10/2004 | Seguin et al. |
| 2004/0260389 A1 | 12/2004 | Case et al. |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2008/0275549 A1* | 11/2008 | Rowe ................ A61F 2/2418 623/2.11 |
| 2008/0288055 A1* | 11/2008 | Paul, Jr. .............. A61F 2/2412 623/1.24 |
| 2009/0099653 A1 | 4/2009 | Suri et al. |
| 2009/0112309 A1 | 4/2009 | Jaramillo et al. |
| 2009/0138071 A1* | 5/2009 | Cheng ................ A61F 2/90 623/1.15 |
| 2009/0138079 A1 | 5/2009 | Tuval et al. |
| 2009/0276027 A1 | 11/2009 | Glynn |
| 2009/0276040 A1* | 11/2009 | Rowe ............... A61B 17/0401 623/2.18 |
| 2010/0004740 A1 | 1/2010 | Seguin et al. |
| 2010/0030244 A1* | 2/2010 | Woolfson ........... A61F 2/2409 606/151 |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249894 A1* | 9/2010 | Oba .................. A61F 2/2418 623/1.11 |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1* | 6/2011 | Chau ................. A61F 2/2418 623/1.11 |
| 2011/0172765 A1 | 7/2011 | Nguyen et al. |
| 2011/0208283 A1 | 8/2011 | Rust |
| 2011/0264206 A1 | 10/2011 | Tabor |
| 2012/0035722 A1 | 2/2012 | Tuval |
| 2012/0078347 A1 | 3/2012 | Braido et al. |
| 2012/0078353 A1* | 3/2012 | Quadri ............... A61F 2/2418 623/2.11 |
| 2012/0101572 A1 | 4/2012 | Kovalsky et al. |
| 2012/0123529 A1 | 5/2012 | Levi et al. |
| 2012/0303116 A1 | 11/2012 | Gorman, III et al. |
| 2013/0274873 A1 | 10/2013 | Delaloye et al. |
| 2014/0121763 A1 | 5/2014 | Duffy et al. |
| 2014/0155997 A1 | 6/2014 | Braido |
| 2014/0214159 A1 | 7/2014 | Vidlund et al. |
| 2014/0228946 A1 | 8/2014 | Chau et al. |
| 2014/0277411 A1* | 9/2014 | Bortlein ............. A61F 2/24 623/2.11 |
| 2014/0303719 A1 | 10/2014 | Cox et al. |
| 2014/0324164 A1 | 10/2014 | Gross et al. |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |

(56) References Cited

U.S. PATENT DOCUMENTS

| | | | | |
|---|---|---|---|---|
| 2014/0371844 A1* | 12/2014 | Dale | ................... | A61F 2/2418 623/2.11 |
| 2016/0030170 A1* | 2/2016 | Alkhatib | ................... | A61F 2/24 623/2.17 |
| 2016/0278923 A1* | 9/2016 | Krans | ................... | A61F 2/2409 |
| 2016/0331529 A1* | 11/2016 | Marchand | ............. | A61F 2/2418 |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 1926455 A2 | 6/2008 |
| EP | 2537487 A1 | 12/2012 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 0149213 A2 | 7/2001 |
| WO | 01054625 A1 | 8/2001 |
| WO | 01056500 A2 | 8/2001 |
| WO | 01076510 A2 | 10/2001 |
| WO | 0236048 A1 | 5/2002 |
| WO | 0247575 A2 | 6/2002 |
| WO | 02067782 A2 | 9/2002 |
| WO | 03047468 A1 | 6/2003 |
| WO | 2005070343 A1 | 8/2005 |
| WO | 06073626 A2 | 7/2006 |
| WO | 07071436 A2 | 6/2007 |
| WO | 08070797 A2 | 6/2008 |
| WO | 10008549 A1 | 1/2010 |
| WO | 10096176 A1 | 8/2010 |
| WO | 10098857 A1 | 9/2010 |

OTHER PUBLICATIONS

"Minimally invasive cardiac surgery", M. J. Mack, Surgical Endoscopy, 2006, 20:S488-S492, DOI: 10.1007/s00464-006-0110-8 (presented Apr. 24, 2006).

"Percutaneous Aortic Valve Implantation Retrograde From the Femoral Artery", John G. Webb et al., Circulation, 2006; 113:842-850 (Feb. 6, 2006).

"Transapical aortic valve implantation: an animal feasibility study"; Todd M. Dewey et al., The annals of thoracic surgery 2006; 82: 110-6 (Feb. 13, 2006).

"Transapical Transcatheter Aortic Valve Implantation in Humans", Samuel V. Lichtenstein et al., Circulation. 2006; 114: 591-596 (Jul. 31, 2006).

Braido et al., Design U.S. Appl. No. 29/375,243, filed Sep. 20, 2010. Is it Reasonable to Treat All Calcified Stenotic Aortic Valves With a Valved Stent?, 579-584, Zegdi, Rachid, MD, PhD at al., J. of the American College of Cardiology, vol. 51, No. 5, Feb. 5, 2008.

Ruiz, Carlos, Overview of PRE-CE Mark Transcatheter Aortic Valve Technologies, Euro PCR—dated May 25, 2010.

Andersen, et al., "Transluminal Implantation of Artificial Heart Valves. Description of a New Expandable Aortic Valve and Initial Results with Implantation by Catheter Technique in Closed Chest Pigs", European Heart Journal, vol. 13, No. 5, May 1992, pp. 704-708.

Andersen, H.R., "Transluminal Catheter Implanted Prosthetic Heart Valves", International Journal of Angiology, vol. 1, No. 2, Mar. 1998, pp. 102-106.

Buellesfeld and Meier, "Treatment of Paravalvular Leaks Through Interventional Techniques", Multimedia Manual of Cardiothoracic Surgery, Department of Cardiology, Ben University Hospital, Jan. 2011, 8 pages.

De Cicco, et al., "Aortic Valve Periprosthetic Leakage: Anatomic Observations and Surgical Results", The Annals of Thoracic Surgery, vol. 79, No. 5, May 2005, pp. 1480-1485.

Gossl and Rihal, "Percutaneous Treatment of Aortic and Mitral Valve Paravalvular Regurgitation", Current Cardiology Reports, vol. 15, No. 8, Aug. 2013, 8 pages.

Heart Advisor, "Heart Repairs Without Surgery. Minimally Invasive Procedures Aim to Correct Valve Leakage", Sep. 2004, PubMed ID 15586429, 2 pages.

Hijazi, et al., "Transcatheter Valve Repair", CRC Press, Jan. 2006, pp. 165-186.

Hourihan, et al., "Transcatheter Umbrella Closure of Valvular and Paravalvular Leaks", Journal of the American College of Cardiology, vol. 20, No. 6, Nov. 1992, pp. 1371-1377.

Knudsen, et al., "Catheter-Implanted Prosthetic Heart Valves: Transluminal Catheter Implantation of a New Expandable Artificial Heart Valve in the Descending Thoracic Aorta in Isolated Vessels and Closed Chest Pigs", The International Journal of Artificial Organs, May 1993, vol. 16, No. 5, pp. 253-262.

Lichtenstein, S.V., "Closed Heart Surgery: Back to the Future", The Journal of Thoracic and Cardiovascular Surgery, vol. 131, No. 5, May 2006, pp. 941-943.

Moazami, et al., "Transluminal Aortic Valve Placement. A Feasibility Study with a Newly Designed Collapsible Aortic Valve", ASAIO Journal (American Society for Artificial Internal Organs: 1992), vol. 42, No. 5, 1996, pp. M381-M385.

Munoz, et al., "Guidance of Treatment of Perivalvular Prosthetic Leaks", Current Cardiology Reports, vol. 16, No. 1, Nov. 2013, 6 pages.

Quaden, et al. "Percutaneous Aortic Valve Replacement: Resection Before Implantation", European Journal of Cardio-Thoracic Surgery, vol. 27, No. 5, May 2005, pp. 836-840.

Rohde, et al., "Resection of Calcified Aortic Heart Leaflets In Vitro by Q-Switched 2 μm Microsecond Laser Radiation", Journal of Cardiac Surgery, vol. 30, No. 2, Feb. 2015, pp. 157-162.

Swiatkiewicz, et al., "Percutaneous Closure of Mitral Perivalvular Leak", Kardiologia Polska (Polish Heart Journal), vol. 67, No. 7, 2009, pp. 762-764.

Walther, et al., "Transapical Approach for Sutureless Stent-Fixed Aortic Valve Implantation: Experimental Results", European Journal of Cardio-Thoracic Surgery, vol. 29, No. 5, Jan. 2006, pp. 703-708.

* cited by examiner

PROSTHETIC MITRAL VALVE

CROSS-REFERENCE TO RELATED APPLICATIONS

This application claims the benefit of the filing date of U.S. Provisional Application No. 62/414,125, filed Oct. 28, 2016, and U.S. Provisional Application No. 62/457,374, filed Feb. 10, 2017, the disclosures of both of which are incorporated herein by reference.

BACKGROUND OF THE INVENTION

The present disclosure relates to heart valve replacement and, in particular, to collapsible prosthetic heart valves. More particularly, the present disclosure relates to collapsible prosthetic heart valves for use in the mitral valve annulus.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve is generally first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

SUMMARY OF THE INVENTION

In some embodiments, a prosthetic heart valve having an inflow end and an outflow end includes a stent having a collapsed condition, an expanded condition, and a plurality of cells arranged in circumferential rows. The stent has an anterior side configured and arranged to be disposed adjacent an anterior native valve leaflet and a posterior side configured and arranged to be disposed adjacent a posterior native valve leaflet. A valve assembly having a plurality of leaflets is disposed within the stent and a flange is disposed about the stent, the flange having a flared portion adjacent the inflow end of the prosthetic heart valve and a body portion extending from the flared portion to the outflow end. The flange extends between a first set of attachment points adjacent the inflow end and a second set of attachment points adjacent the outflow end.

In some embodiments, a prosthetic heart valve having an inflow end and an outflow end includes a stent having a collapsed condition, an expanded condition, and a plurality of cells arranged in circumferential rows. The stent has an anterior side configured and arranged to be disposed adjacent an anterior native valve leaflet and a posterior side configured and arranged to be disposed adjacent a posterior native valve leaflet. A valve assembly having a plurality of leaflets is disposed within the stent and a flange is disposed about the stent, the flange being asymmetric about a longitudinal axis such that a posterior side of the flange has a different shape than an anterior side of the flange.

BRIEF DESCRIPTION OF THE DRAWINGS

Various embodiments of the present disclosure are described herein with reference to the drawings, wherein.

DETAILED DESCRIPTION

Blood flows through the mitral valve from the left atrium to the left ventricle. As used herein, the term "inflow end," when used in connection with a prosthetic mitral heart valve, refers to the end of the heart valve closest to the left atrium when the heart valve is implanted in a patient, whereas the term "outflow end," when used in connection with a prosthetic mitral heart valve, refers to the end of the heart valve closest to the left ventricle when the heart valve is implanted in a patient. Also, as used herein, the terms "substantially," "generally," and "about" are intended to mean that slight deviations from absolute are included within the scope of the term so modified. Generally, materials described as being suitable for components in one embodiment of the disclosure may also be suitable for similar or identical components described in other embodiments.

Figure 1:
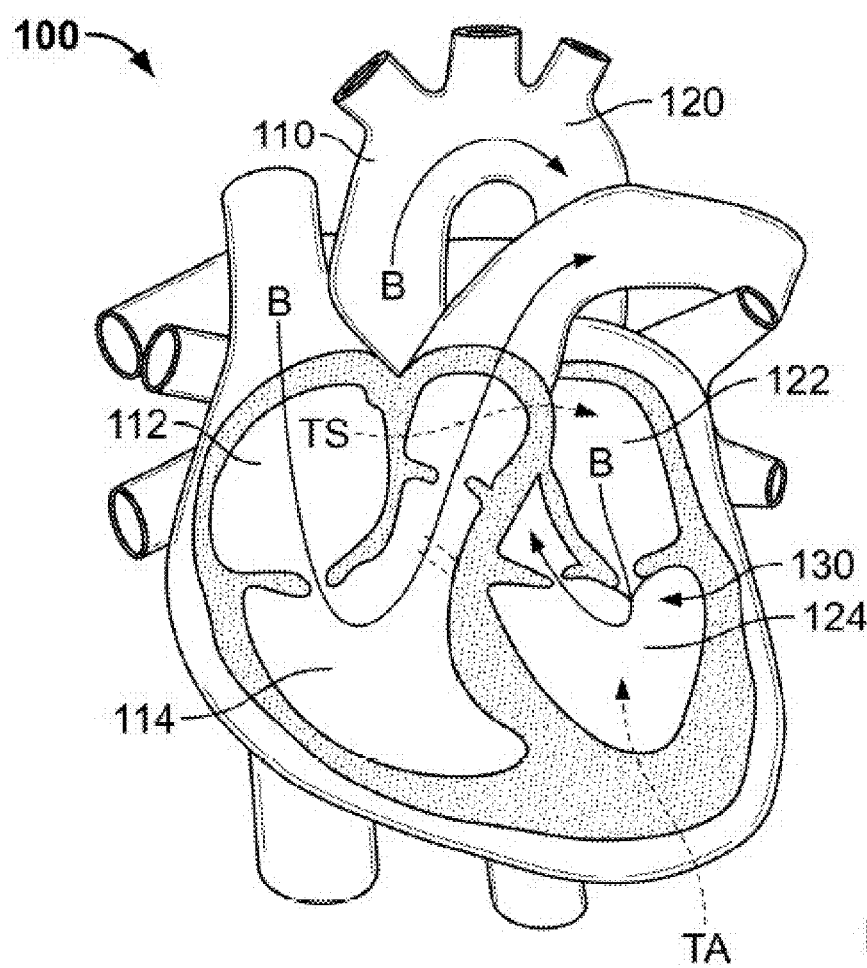
FIG. 1 is a highly schematic cutaway representation of a human heart showing various delivery approaches.

FIG. 1 is a highly schematic cutaway representation of human heart 100. The human heart includes two atria and two ventricles: right atrium 112 and left atrium 122, and right ventricle 114 and left ventricle 124. Heart 100 further includes aorta 110 and aortic arch 120. Disposed between left atrium 122 and left ventricle 124 is mitral valve 130. Mitral valve 130, also known as the bicuspid valve or left atrioventricular valve, is a dual-flap valve that opens as a result of increased pressure in left atrium 122 as it fills with blood. As atrial pressure increases above that of left ventricle 124, mitral valve 130 opens and blood passes into left ventricle 124. Blood flows through heart 100 in the direction shown by arrows "B".

A dashed arrow, labeled "TA", indicates a transapical approach for implanting a prosthetic heart valve, in this case to replace the mitral valve. In transapical delivery, a small incision is made between the ribs and into the apex of left ventricle 124 to deliver the prosthetic heart valve to the target site. A second dashed arrow, labeled "TS", indicates a transseptal approach for implanting a prosthetic heart valve in which the valve is passed through the septum between right atrium 112 and left atrium 122. Other approaches for implanting a prosthetic heart valve are also possible.

Figure 2:
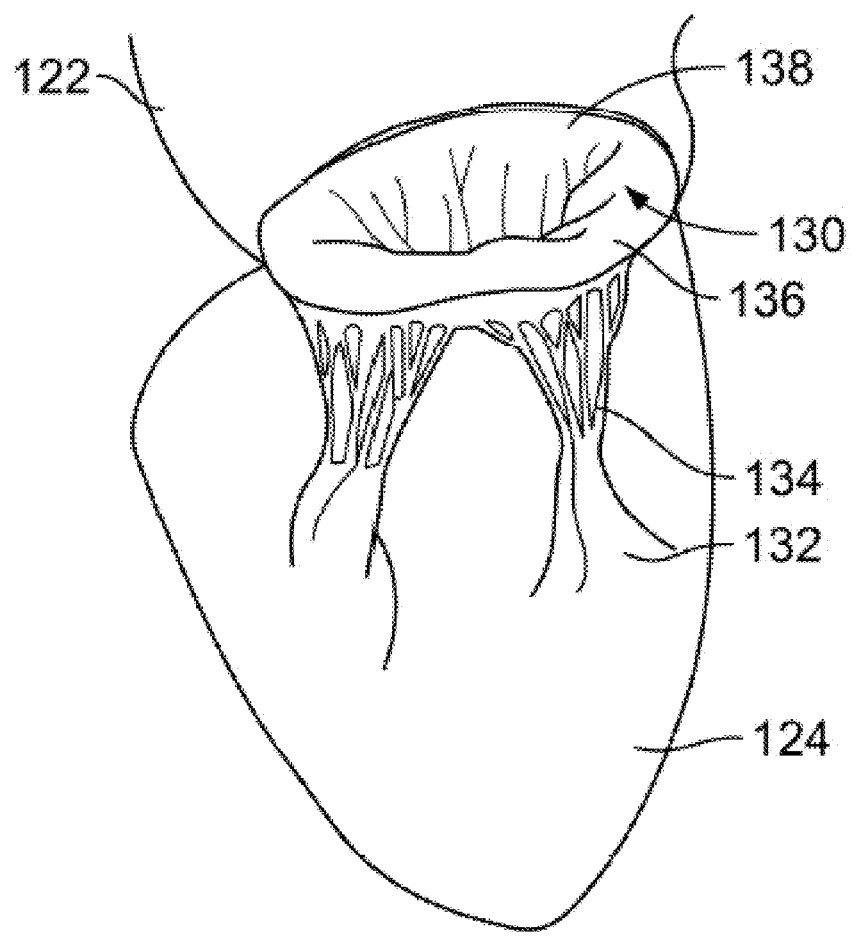
FIG. 2 is a highly schematic representation of a native mitral valve and associated cardiac structures.

FIG. 2 is a more detailed schematic representation of native mitral valve 130 and its associated structures. As previously noted, mitral valve 130 includes two flaps or leaflets, posterior leaflet 136 and anterior leaflet 138, disposed between left atrium 122 and left ventricle 124. Cord-like tendons, known as chordae tendineae 134, connect the two leaflets 136, 138 to the medial and lateral papillary muscles 132. During atrial systole, blood flows from higher pressure in left atrium 122 to lower pressure in left ventricle 124. When left ventricle 124 contracts in ventricular systole, the increased blood pressure in the chamber pushes leaflets 136, 138 to close, preventing the backflow of blood into left atrium 122. Since the blood pressure in left atrium 122 is much lower than that in left ventricle 124, leaflets 136, 138 attempt to evert to the low pressure regions. Chordae tendineae 134 prevent the eversion by becoming tense, thus pulling on leaflets 136, 138 and holding them in the closed position.

Figure 3A:
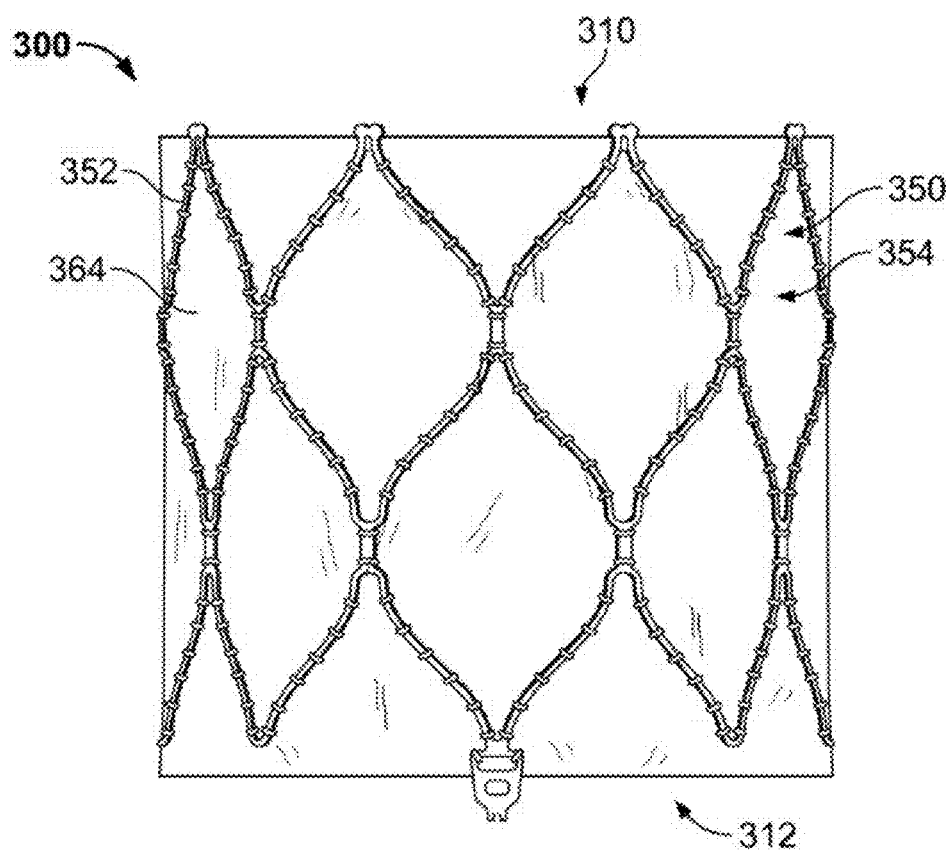
FIG. 3A is a side view of a prosthetic heart valve according to the prior art.
Figure 3B:
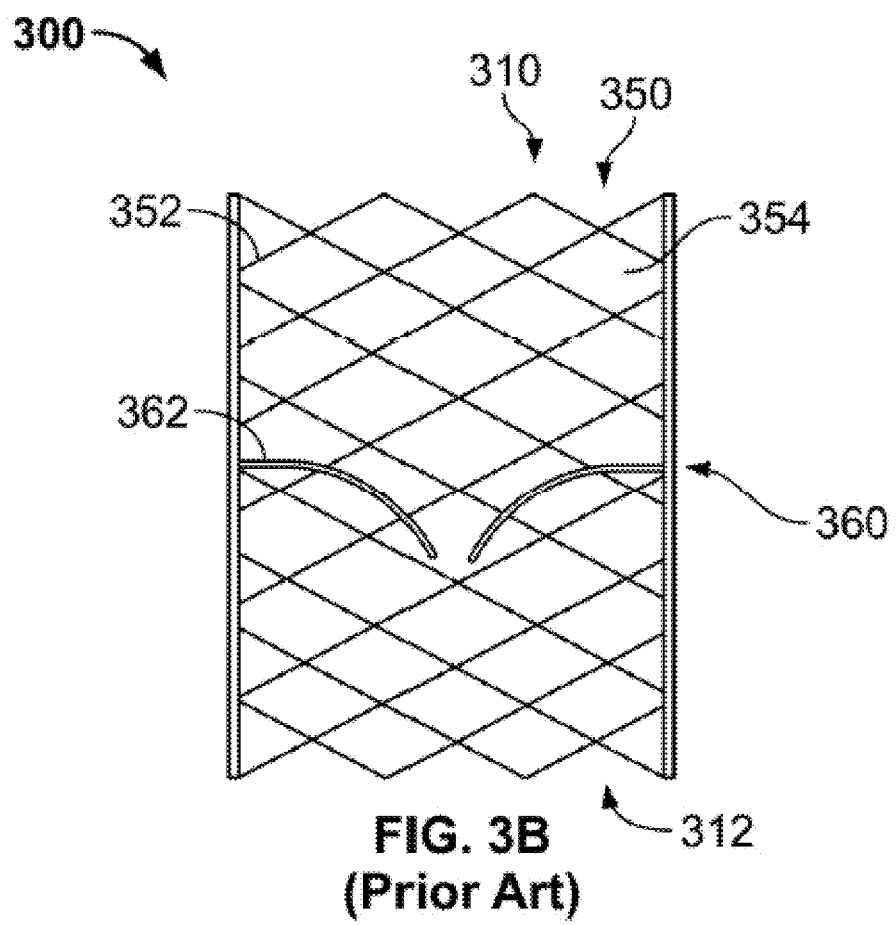
FIG. 3B is a highly schematic longitudinal cross-section of the prosthetic heart valve of FIG. 3A.

FIGS. 3A and 3B are a side view and a longitudinal cross-sectional view of prosthetic heart valve 300 according to the prior art. Prosthetic heart valve 300 is a collapsible prosthetic heart valve designed to replace the function of the native mitral valve of a patient (see native mitral valve 130 of FIGS. 1-2). Generally, prosthetic valve 300 has a substantially cylindrical shape with inflow end 310 and outflow end 312. When used to replace native mitral valve 130, prosthetic valve 300 may have a low profile so as not cause obstruction of the left ventricle outflow tract.

Prosthetic heart valve 300 may include stent 350, which may be formed from biocompatible materials that are capable of self-expansion, such as, for example, shape-memory alloys including nitinol. Stent 350 may include a plurality of struts 352 that form cells 354 connected to one another in one or more annular rows around the stent. Cells 354 may all be of substantially the same size around the perimeter and along the length of stent 350. Alternatively, cells 354 near inflow end 310 may be larger than the cells near outflow end 312. Stent 350 may be expandable to provide a radial force to assist with positioning and stabilizing prosthetic heart valve 300 in the native valve annulus.

Prosthetic heart valve 300 may also include a substantially cylindrical valve assembly 360 including a plurality of leaflets 362 (FIG. 3B) attached to a cuff 364 (FIG. 3A). Leaflets 362 replace the function of native mitral valve leaflets 136 and 138 described above with reference to FIG. 2. That is, leaflets 362 coapt with one another to function as a one-way valve. The valve assembly 360 of prosthetic heart valve 300 may include two or three leaflets, but it should be appreciated that prosthetic heart valve 300 may have more than three leaflets. Both cuff 364 and leaflets 362 may be wholly or partly formed of any suitable biological material, such as bovine or porcine pericardium, or polymers, such as polytetrafluoroethylene (PTFE), urethanes and the like. Valve assembly 360 may be secured to stent 350 by suturing to struts 352 or by using tissue glue, ultrasonic welding, or other suitable methods.

When prosthetic heart valve 300 is implanted in a patient, for example at the annulus of native mitral valve 130, it is biased towards an expanded condition, providing radial force to anchor the valve in place. However, if the radial force is too high, damage may occur to heart tissue. If, instead, the radial force is too low, the heart valve may move from its implanted position, for example, into either left ventricle 124 or left atrium 122, requiring emergency surgery to remove the displaced valve. The potential for such movement may be heightened in mitral valve applications, particularly if a low profile valve is used.

Another potential issue with prosthetic heart valves is inadequate sealing between the prosthetic valve and the native tissue. For example, if prosthetic heart valve 300 is implanted at the annulus of mitral valve 130 in a patient, improper or inadequate sealing may result in blood flowing from left ventricle 124 into left atrium 122, even if leaflets 362 of valve assembly 360 are working properly. This may occur, for example, if blood flows in a retrograde fashion between the outer perimeter of prosthetic heart valve 300 and the native tissue at the site of implantation. This phenomenon is known as perivalvular (or paravalvular) leak ("PV leak").

In addition to anchoring and perivalvular leakage, there are other considerations when forming a prosthetic heart valve for mitral applications. For example, the replacement valve may need to accommodate irregular or large mitral valve annuli without damaging nearby native structures or affecting electrical signals. Additionally, the replacement valve may address the location and position of the left ventricular outflow tract and try to limit obstruction of it. The replacement valve should also be simple to use and the ability of the valve to anchor within the native annulus should be easy and repeatable.

Other considerations may include the anchoring or securement of the posterior leaflet. Because of the relatively small size and location of the posterior leaflet in some patients, it may be difficult to visualize and capture the leaflet with an anchor. It would also be beneficial to reduce the risk of migration of the valve. Additionally, it would be beneficial to secure the native leaflets so that they do not obstruct blood flow, for example, into the left ventricular outflow tract or the aorta.

Figure 4A:
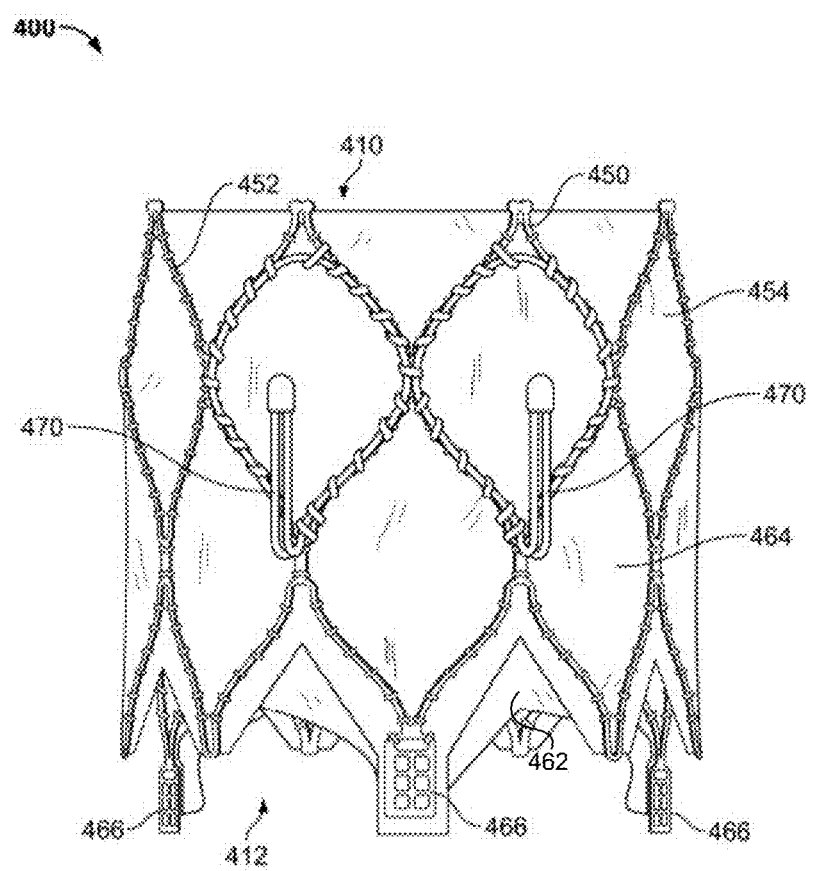
FIG. 4A is a side view of a prosthetic heart valve according to an aspect of the disclosure.

FIG. 4A is a side view of a prosthetic heart valve 400 in accordance with one embodiment of the disclosure. Prosthetic heart valve 400 may be similar or identical to prosthetic heart valve 300 in certain respects. For example, prosthetic heart valve 400 is collapsible and expandable and designed to replace a native mitral valve, having a substantially cylindrical shape with an inflow end 410 and an outflow end 412. It should be understood that prosthetic heart valve 400 is not limited to replacement of mitral valves, and may be used to replace other heart valves. Prosthetic heart valve 400 may include stent 450, which may be similar to stent 350, having a plurality of struts 452 that form cells 454 connected to one another in one or more annular rows around stent 450. Stent 450 includes two annular rows of cells 454 of substantially similar size and shape, with nine cells in each row. As illustrated, cells 454 are generally diamond shaped. However, it should be understood that a different number of rows of cells 454, as well as a different number of cells 454 per row, may be suitable. As discussed in relation to stent 350, stent 450 may be formed from a shape memory alloy, such as nitinol. The struts 452 forming stent 450 may have a diameter of between about 0.020 inches (0.51 mm) and about 0.025 inches (0.64 mm), although other dimensions may be suitable. Forming stent 450 from struts 452 of a relatively large diameter may provide increased stiffness to stent 450, which may provide certain benefits, such as minimizing the deflection of commissure attachment features (CAFs) 466 during normal operation of prosthetic heart valve 400. On the other hand, forming stent 450 from struts 452 of a relatively small diameter may provide increased flexibility to stent 450, which may provide certain benefits, such as the capability to be collapsed to a smaller profile during delivery.

Prosthetic heart valve 400 may also include a valve assembly having three leaflets 462 attached to a cylindrical cuff 464 similar to that shown and described with reference to FIGS. 3A-B. It should be understood that although native mitral valve 130 has two leaflets 136, 138, prosthetic heart valve 400 may have three leaflets 462, or more or fewer than three leaflets, provided that the leaflets act to allow one-way antegrade blood flow through the prosthetic heart valve 400, but obstruct retrograde blood flow through the prosthetic heart valve. Prosthetic heart valve 400 may have the same number of leaflets 462 as CAFs 466, each CAF providing a point of attachment for adjacent leaflets to stent 450. It should be understood that prosthetic heart valve 400 may alternatively include a pair of prosthetic leaflets and a corresponding pair of CAFs.

As with stent 350, stent 450 may be expandable to provide a radial force to assist with positioning and stabilizing prosthetic heart valve 400 in the native mitral valve annulus. However, prosthetic valve 400 includes additional securement features in the form of anchor arms 470 to help prevent prosthetic heart valve 400 from migrating into left atrium 122. Anchor arms 470 may be separately attachable such that they hook under native mitral valve leaflets 136, 138 or may be cut directly into the stent 450, for example, via laser cutting.

Figure 4B:
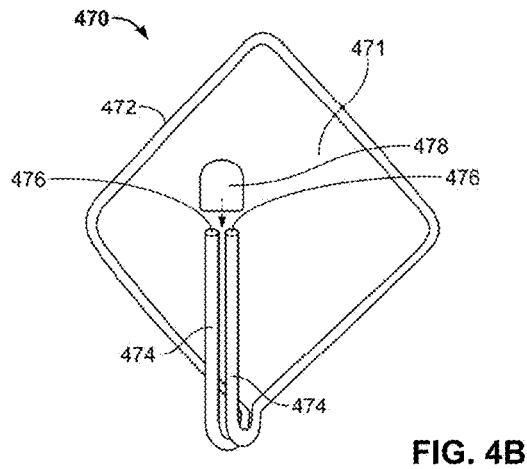
FIG. 4B is an isolated perspective view of an anchor feature of the prosthetic heart valve of FIG. 4A.

A single anchor arm 470 is shown in FIG. 4B. Anchor arm 470 may be formed of a single wire 472 bent or otherwise formed into a body portion 471 having a substantially diamond shape. Wire 472 is preferably a shape-memory alloy such as nitinol. In one example, wire 472 is formed of nitinol having a diameter of about 0.015 inches (0.38 mm). As with struts 452 of stent 450, the diameter of wire 472 may be increased to provide increased stiffness or decreased to provide increased flexibility. Although the shape of body portion 471 may vary, it preferably corresponds to the geometry of a single cell 454 of stent 450. Wire 472 has two free end portions 474 that extend adjacent and substantially parallel to one another, and that are curved or hooked so as to lie at a spaced distance radially outward from body portion 471. Preferably, the tip 476 of each free end portion 474 is blunt and/or rounded to reduce the likelihood of tips 476 damaging the native tissue hooked by anchor arm 470. In addition or alternatively, a blunted and/or rounded end cap 478 may be assembled over or onto the tips 476 of free end portions 474 and fixed to tips 476, for example by welding, to provide an atraumatic tissue contact surface.

Figure 4C:
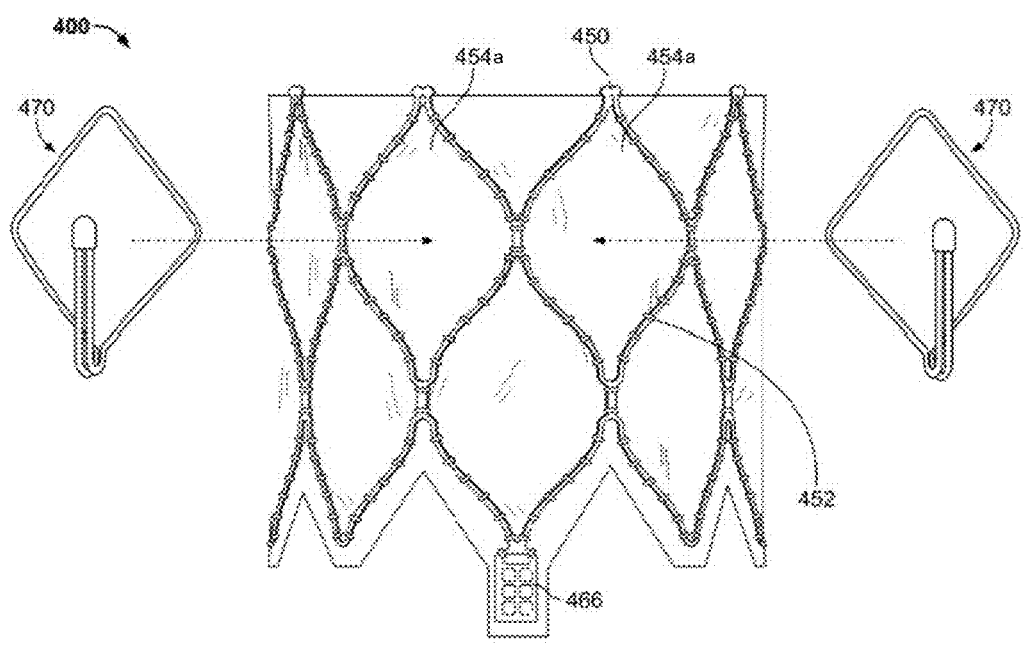
FIG. 4C is a side view of the prosthetic heart valve of FIG. 4A in a stage of manufacture.

Prosthetic heart valve 400 is shown at a possible intermediate stage of manufacture in FIG. 4C to better illustrate the attachment of anchor arms 470 to prosthetic heart valve 400. After cuff 464 and leaflets 462 have been attached to stent 450, anchor arms 470 may be coupled to prosthetic heart valve 400 at desired locations around stent 450. As shown in FIG. 4C, anchor arms 470 may be positioned within and/or adjacent to a selected cell 454a of stent 450 and connected to the prosthetic heart valve 400, for example by suturing body portion 471 of anchor arm 470 to the struts 452 defining the perimeter of selected cell 454a. The sutures coupling anchor arms 470 to prosthetic heart valve 400 may additionally pass through cuff 464. Forces applied to free end portions 474 are transmitted to the body portion 471 of anchor arm 470. With the above-described configuration of anchor arm 470 and its attachment to cell 454a, those transmitted forces are distributed over a larger area of stent 450, providing better reinforcement than if free end portions 474 were sewn or otherwise directly connected to stent 450 without the use of body portion 471.

Figure 4D:
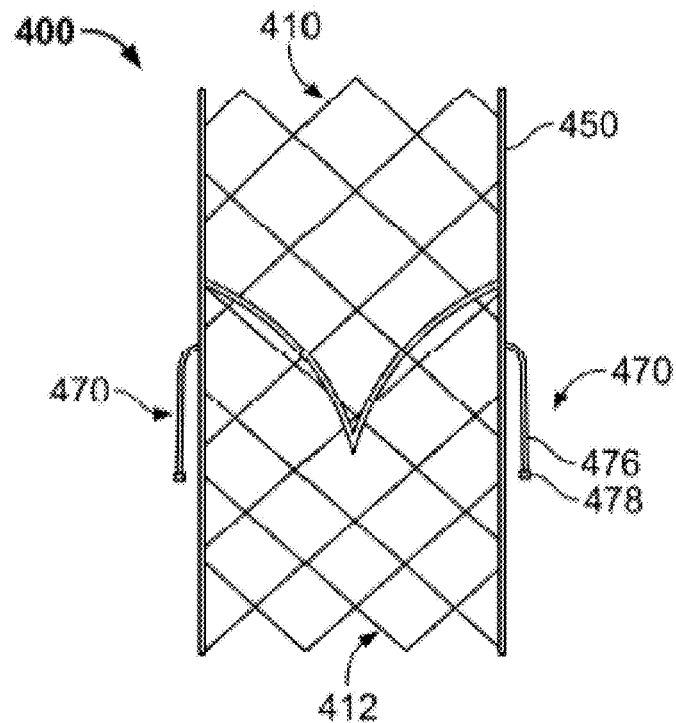
FIG. 4D is a highly schematic longitudinal cross-section of the prosthetic heart valve of FIG. 4A in a collapsed condition.
Figure 4E:
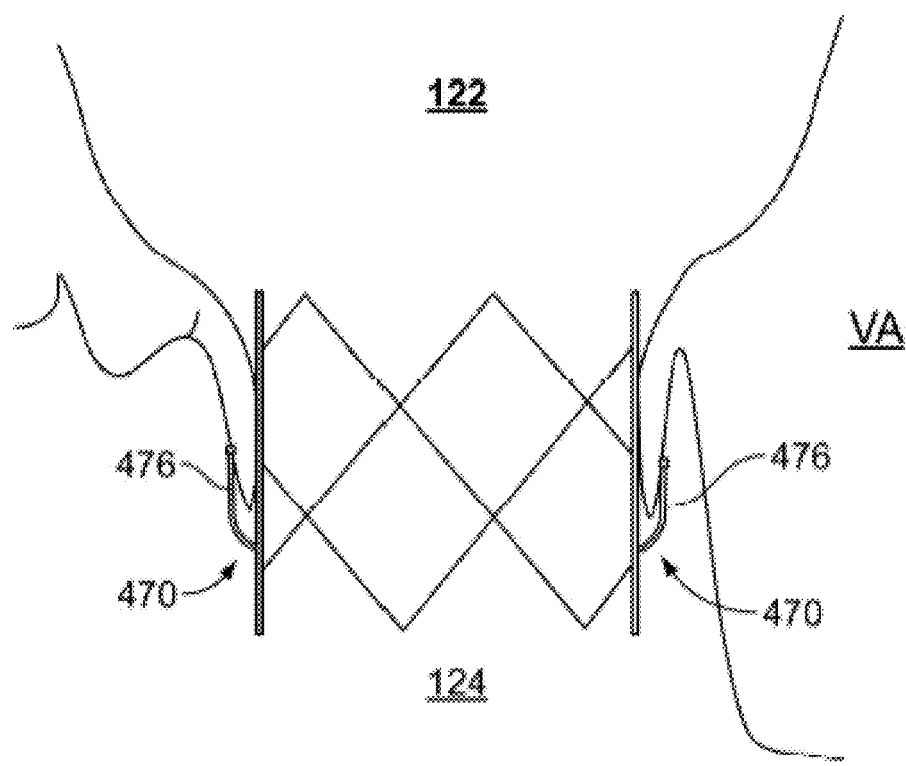
FIG. 4E is a highly schematic representation of the prosthetic heart valve of FIG. 4A implanted into a native mitral valve annulus.

As noted above, wire 472 forming anchor arms 470 is preferably made from a shape-memory alloy. By using a shape-memory alloy, the shape of anchor arms 470 may be set, for example by heat setting, to take the illustrated shape in the absence of applied forces. However, forces may be applied to anchor arms 470 and to prosthetic heart valve 400 generally to reduce the radial size and/or bulk of the prosthetic heart valve when in the collapsed condition, which may facilitate intravascular (or other minimally invasive) delivery of the prosthetic heart valve via a delivery device (not shown). For example, as shown in FIG. 4D, prosthetic heart valve 400 may be transitioned to the collapsed condition, with free end portions 474 of anchor arms 470 being distorted or "flipped" to point toward outflow end 412 rather than inflow end 410. Prosthetic heart valve 400 may be maintained in the collapsed condition, for example by a surrounding sheath of a delivery device (not shown), as prosthetic heart valve 400 is delivered to native mitral valve 130. When in a desired position relative to native mitral valve 130, prosthetic heart valve 400 may be released from the delivery device. As the constraining forces are removed from prosthetic heart valve 400, it begins to transition to the expanded condition, while anchor arms 470 move to their preset shape. Since anchor arms 470 are shape-set so that their free end portions 474 point toward inflow end 410, anchor arms 470 revert to that shape when released from the delivery device. As the free end portions 474 of anchor arms 470 transition from pointing toward outflow end 412 to pointing toward inflow end 410, native mitral valve leaflets 136, 138 are captured between the free end portions 474 and the body of stent 450, as shown in FIG. 4E. When hooked around native mitral valve leaflets 136, 138, anchor arms 470 help anchor prosthetic heart valve 400 within native valve annulus VA and are particularly effective at resisting migration of the prosthetic heart valve into left atrium 122. Distorting or flipping the anchor arms 470 while prosthetic heart valve 400 is maintained in the collapsed condition may reduce the profile of the collapsed valve, although prosthetic heart valve 400 may alternatively be put in the collapsed condition without distorting or flipping anchor arms 470.

As described above, the stent 450 of prosthetic heart valve 400 may include two circumferential rows of annular cells 454, with each row containing nine such cells. Although the use of nine cells 454 per row is merely an example, the use of an odd number of cells 454 per row in prosthetic heart valves for replacing native mitral valve 130 may cause difficulty in creating symmetry in the positioning of anchor arms 470 on the prosthetic heart valve.

While prosthetic heart valve 400 may be used as shown and described above in connection with FIGS. 4A-E, a prosthetic heart valve may be provided with additional anchoring and/or sealing elements. For example, FIGS. 5A-D illustrate a prosthetic heart valve 500 that essentially comprises prosthetic heart valve 400 with a flange 580 coupled thereto. This embodiment has many elements that perform functions analogous to like-numbered elements of the previous embodiment, these elements having a leading digit of "5" instead of a "4", so that elements 500, 510, 512, 550, 552, 554, 566, and the like are analogous to previously-described elements 400, 410, 412, 450, 452, 454, 466, etc. It will be noted that stent 550 is similar to stent 450, but includes a plurality of anchor arms 570 extending therefrom. In one embodiment, a pair of anchor arms 570 may be provided on a portion of the stent 550, for example, on the anterior side thereof, as is further described in later embodiments, additionally or alternatively, a plurality of anchor arms 570 may be disposed circumferentially around the stent 550 as shown in FIG. 5.

Figure 5A:
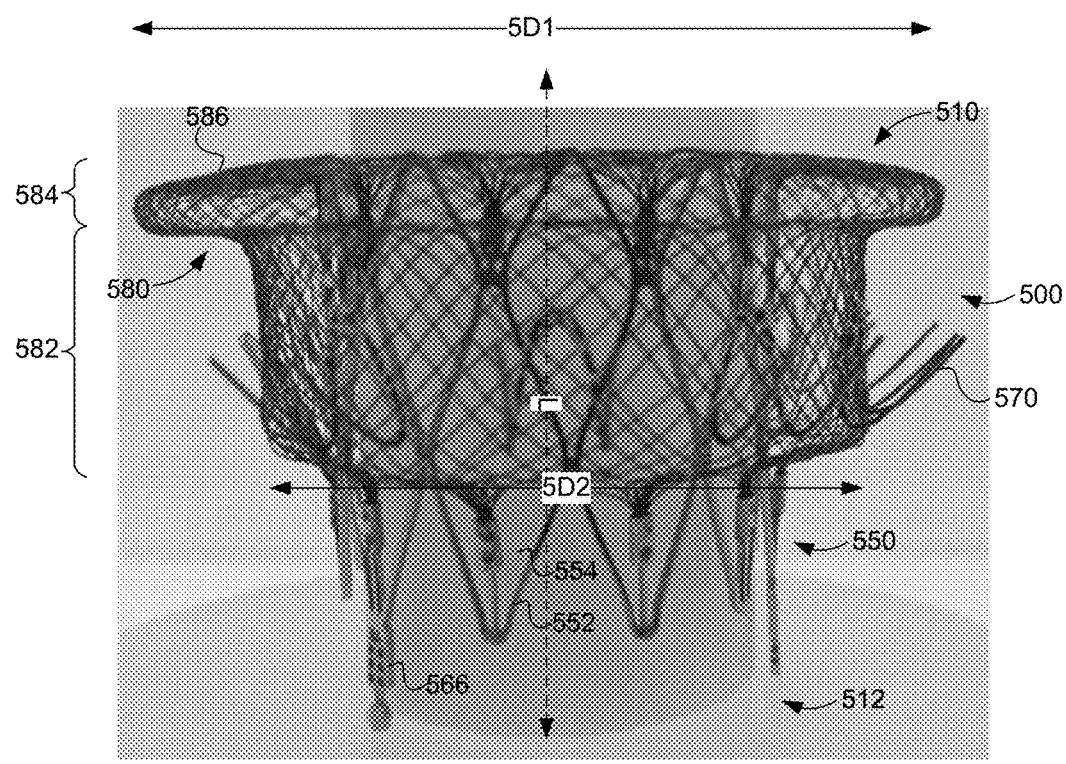
FIG. 5A is a side view of a prosthetic heart valve according to a further aspect of the disclosure.

Additionally, prosthetic heart valve 500 includes flange 580 to facilitate the anchoring of the heart valve within native mitral valve annulus 130 and the prevention of PV leak. Flange 580 may be formed of a material braided to create various shapes and/or geometries to engage tissue. As shown in FIG. 5A, flange 580 includes a plurality of braided strands or wires 586 arranged in three-dimensional shapes. In one example, wires 586 form a braided metal fabric that is resilient, collapsible and capable of heat treatment to substantially set a desired shape. One class of materials which meets these qualifications is shape-memory alloys, such as nitinol. Wires 586 may comprise various materials other than nitinol that have elastic and/or memory properties, such as spring stainless steel, tradenamed alloys such as Elgiloy® and Hastelloy®, CoCrNi alloys (e.g., tradename Phynox), MP35N®, CoCrMo alloys, or a mixture of metal and polymer fibers. Depending on the individual material selected, the strand diameter, number of strands, and pitch may be altered to achieve the desired shape and properties of flange 580.

Figure 5B:
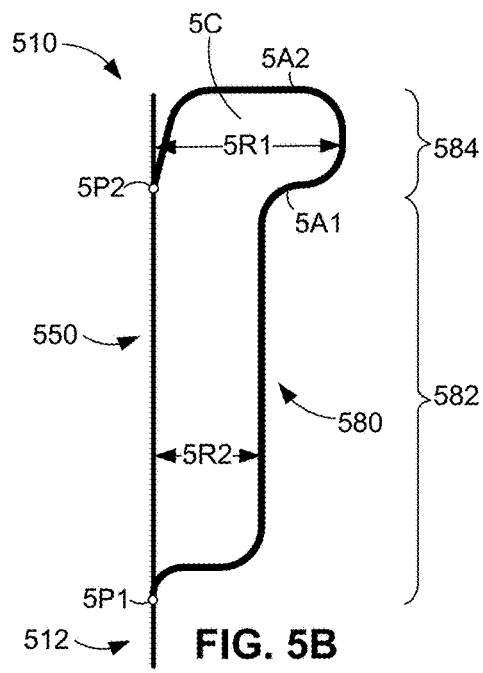
FIG. 5B is a schematic profile view of the prosthetic heart valve of FIG. 5A.

Flange 580 may include a body portion 582 terminating at an outflow end of the flange and a flared portion 584 terminating at an inflow end of the flange. Body portion 582 may be formed with a generally cylindrical or tubular geometry and may be configured to be circumferentially disposed around a portion of stent 550 and/or valve assembly 560. Flange 580 may be coupled to stent 550 (and optionally to the leaflets and/or cuff) by sutures, for example. Flange 580 may be alternatively or additionally connected to stent 550 via a coupler, ultrasonic welds, laser welding, glue, adhesives, or other suitable means. In one particular embodiment, the wires 586 of the flange 580 are collected in marker bands and welded in groups, for example in a quantity of 12, although alternative quantities are possible. A coupler tube, formed of stainless steel, nitinol, platinum/iridium, MP35N, titanium, or the like, with corrosion resistance and suitable weld strength properties, may then be welded, for example, via a laser, to a strut 552 of the stent. As shown in the profile of FIG. 5B, flange 580 may be connected to stent 550 at attachment position 5P1, may flare out slightly to form a generally tubular body portion 582, bulge out to form flared portion 584 and fold over itself to couple to stent 550 at attachment position 5P2. At each attachment position 5P1, 5P2 a number of strands of the wires 586 forming flange 580 may be tied or crimped together and attached to the strut 552 of stent 550. By having multiple attachment positions (e.g., 5P1 adjacent outflow end 512 and 5P2 adjacent inflow end 510) a three-dimensional structure may be formed, the structure having two portions 5A1, 5A2 of braided material at least partially overlapping one another to form flange 580, the two portions defining a cavity 5C therebetween.

When coupled to stent 550, body portion 582 of flange 580 is nearer outflow end 512 and flared portion 584 is nearer inflow end 510. In the expanded condition, flared portion 584 extends a greater distance radially outwardly from the longitudinal axis L of prosthetic heart valve 500 than body portion 582. In other words, as shown in FIG. 5A, flared portion 584 may have a diameter 5D1 that is greater than the diameter 5D2 of body portion 582 when prosthetic heart valve 500 is in the expanded condition. In at least some examples, diameter 5D1 may be between 50 and 70 mm, while diameter 5D2 may be between 40 and 60 mm. Moreover, as shown in FIG. 5B, flared portion 584 may radially extend a distance 5R1 from the stent, while body portion 582 may radially extend a distance 5R2 from the stent. In at least some examples, distance 5R1 may be between 10 and 25 mm, while distance 5R2 may be between 5 and 15 mm.

Flange 580 may be preset to take the illustrated shape in the absence of external forces. As with stent 450 and anchor arms 470 of FIG. 4A, flange 580 may be collapsed to a decreased profile to facilitate minimally invasive delivery. For example, prosthetic heart valve 500 may be transitioned from the expanded condition to the collapsed condition and maintained in the collapsed condition by a surrounding sheath of a delivery device.

Prosthetic heart valve 500 may be delivered to the implant site in the collapsed condition and, when in the desired position relative to native mitral valve 130, transitioned to the expanded condition, for example by removing the surrounding sheath of the delivery device. During the transition from the collapsed condition to the expanded condition, anchor arms 570 revert to the preset shape, capturing native mitral valve leaflets 136, 138 between anchor arms 570 and corresponding portions of stent 550. Flange 580 also transitions from the collapsed condition to the expanded condition, assuming its preset shape. When implanted and in the expanded condition, flange 580 provides a large surface area to help anchor prosthetic valve 500 within the native valve annulus, and may be particularly effective at resisting movement of prosthetic heart valve 500 toward left ventricle 124. Specifically, flange 580 is sized to have an expanded diameter that is too large to pass through the native valve annulus. Because flange 580 is coupled to stent 550, prosthetic heart valve 500 is restricted from migrating into left ventricle 124 during normal operation of prosthetic heart valve 500. Thus, the combination of anchor arms 570 engaged with the mitral valve leaflets, and flange 580 engaged with the tissue on the atrial side of the mitral valve annulus, helps to securely anchor prosthetic heart valve 500 within the mitral valve annulus and limits its migration toward either the left atrium or the left ventricle.

Figure 5C:
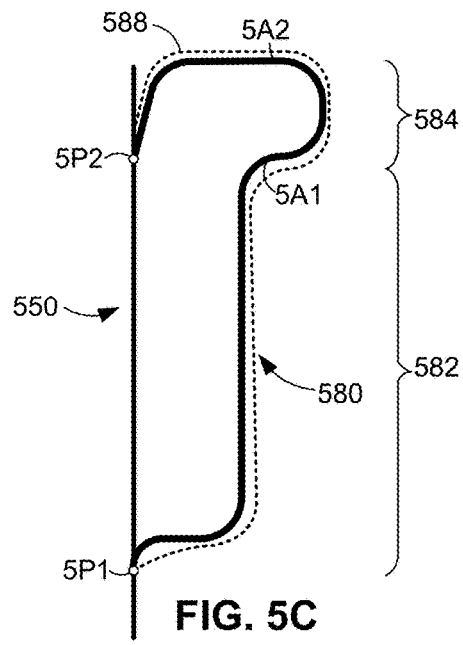
FIG. 5C is a schematic profile view of a variant of the prosthetic heart valve of FIG. 5A having a covering layer.
Figure 5D:
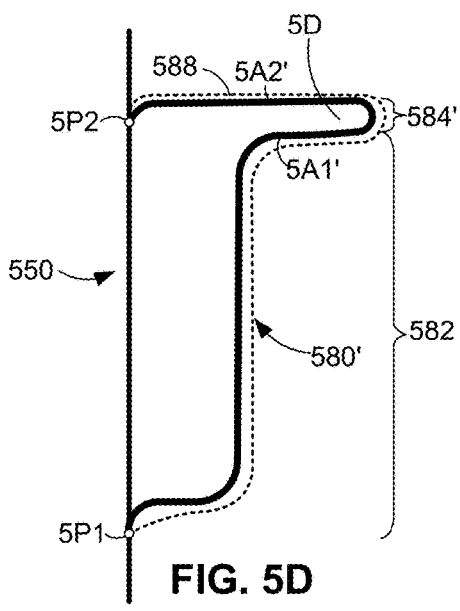
FIG. 5D is a schematic profile view of another variant of the prosthetic heart valve of FIG. 5A having a covering layer.

In addition to providing anchoring capabilities, flange 580 may improve sealing between prosthetic heart valve 500 and the native valve annulus. For example, a covering layer 588, such as a polyester fabric or tissue, may be placed over portions 5A1,5A2 of flange 580 (FIG. 5C). Alternatively, only a portion of flange 580 may be covered with covering layer 588 (e.g., only portion 5A1, only portion 5A2 or only a fraction of portions 5A1, 5A2). Covering layer 588 may enhance tissue ingrowth into prosthetic heart valve 500 after implantation and may also enhance the fluid seal, and thus help prevent PV leak, between the outer diameter of prosthetic heart valve 500 and the adjacent portions of the native mitral valve annulus. In a variation hereof, a covering layer 588 may be applied to the inside surface of flange 580, or to both the outside and inside surfaces of flange 580 to improve sealing between prosthetic heart valve 500 and the native valve annulus. In another variation, shown in FIG. 5D, portions 5A1',5A2' of flange 580' are disposed closer together and cavity 5D is formed, which is smaller than cavity 5C, resulting in a flared portion 584' that is flatter than that described above.

Figure 6A:
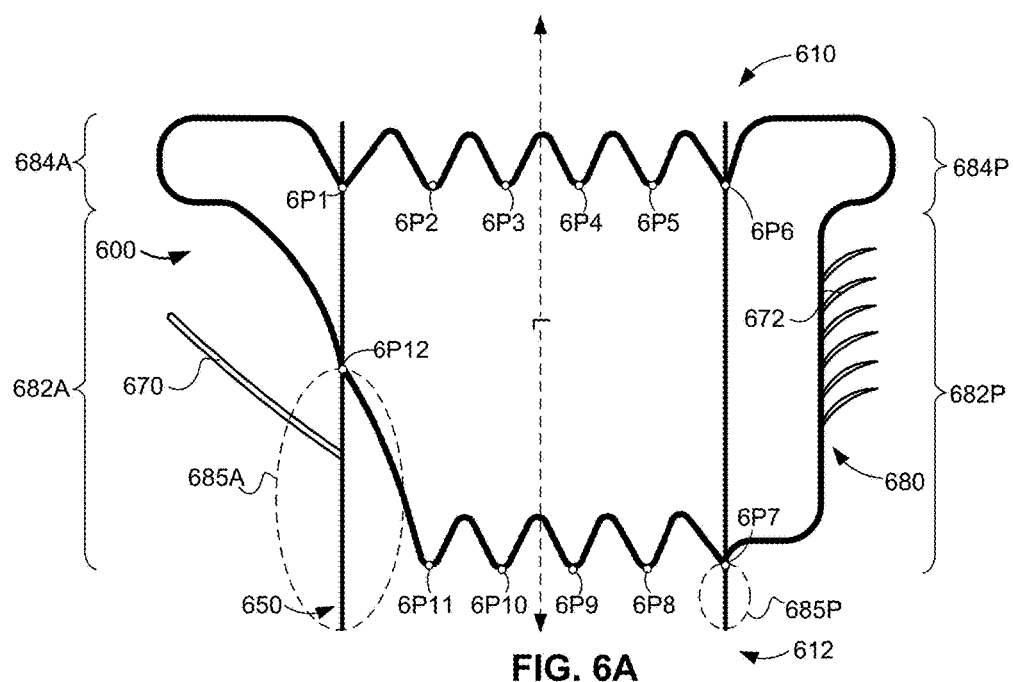
FIG. 6A is a side view of a prosthetic heart valve according to yet another aspect of the disclosure.

FIG. 6A is a schematic cross-sectional view of prosthetic heart valve 600 in accordance with a further embodiment of the disclosure. Prosthetic heart valve 600 may be similar to prosthetic heart valve 500 in certain respects. For example, prosthetic heart valve 600 is collapsible and expandable and designed for replacement of a native mitral valve, having a substantially cylindrical shape with an inflow end 610 and an outflow end 612. Prosthetic heart valve 600 may also include a valve assembly (not shown) having three leaflets attached to a cylindrical cuff in substantially the same manner as described above in connection with previously-described prosthetic valves. It should be understood that prosthetic heart valve 600 is not limited to replacement of mitral valves, and may be used to replace other heart valves.

Prosthetic heart valve 600 may include stent 650, which generally extends between inflow end 610 and outflow end 612 and includes a plurality of struts forming rows of cells. CAFs (not shown) may be included near outflow end 612 for coupling the leaflets to the stent. Prosthetic heart valve 600 may also include a flange 680 similar to flange 580 described above, and formed of any of the materials described, such as braided nitinol wires.

In contrast to the previous embodiments, flange 680 has an asymmetric configuration about a central longitudinal axis L of prosthetic heart valve 600. Specifically, the flange forms different shapes on the anterior and posterior sides of the prosthetic heart valve. On the posterior side, flange 680 has a flared portion 684P and a body portion 682P that are similar to those of FIGS. 5A-B. It is of note that body portion 682P may terminate before the extreme end of the outflow end 612 of the valve so as not cover all of stent 650, and that an exposed portion 685P of stent 650 may be formed at the outflow end 612 on the posterior side of the valve.

Conversely, on the anterior side of the prosthetic heart valve, flange 680 has the same or similar flared portion 684A, but a different body portion 682A which leaves an exposed portion 685A of stent 650 that is much larger than exposed portion 685P. Specifically, body portion 682A is formed such that only about half of stent 650 is covered by flange 680 on the anterior side. In at least some examples, exposed portion 685A of stent 650 is between about 10% and about 80% of the total length of stent 650 in the fully expanded condition, or between about 30% and about 60% of the total length of stent 650. Additionally, the coverage of flange 680 may be determined by the location of its points of attachment to stent 650. For example, in the example shown in FIG. 6A, twelve attachment points are shown, six attachment points 6P1-6P6 near inflow end 610 and six attachment points 6P7-6P12 defining the extent to which flange 680 extends toward outflow end 612. As shown in FIG. 6A, five of the lower attachment points 6P7-6P11 are generally aligned in the circumferential direction of stent 650, while the sixth attachment point 6P12 is disposed approximately halfway between inflow end 610 and outflow end 612. It will be understood that the number of attachment points may be varied to include two, three, four, five, six, seven, eight, nine, ten or more attachment points, but that the attachment points on the anterior side may be intentionally misaligned with the attachment points on the posterior side of the valve to form the intended exposed portions. In some other examples, the number of attachment points in a row is equal to the number of cells in one row of the stent, each attachment point corresponding to one cell in the row.

The relatively large exposed portion 685A at the anterior side of the stent permits uninterrupted blood flow and avoids obstruction of the left ventricular outflow tract. To further assist in limiting obstruction of the left ventricular outflow tract, one or more anchor arms 670 may be disposed adjacent exposed portion 685A to retain the native valve leaflet in place during operation of the valve and further prevent the native valve leaflet from moving toward the left ventricular outflow tract. Conversely, on the posterior side, a plurality of stabilizing wires 672 may be used instead of an anchoring arm. In fact, stabilizing wires 672 may be disposed circumferentially around flange 680 at all locations. The stabilizing wires 672, which may be in the form of a hook or a barb, push against or pierce native tissue during radial expansion to further stabilize the prosthetic heart valve. Because the posterior native leaflet and the anterior native leaflet have different sizes and geometries, the use of a combination of stabilizing wires and anchor arms may yield better anchoring than a symmetric configuration. For example, the shorter native posterior leaflet may be more easily grasped with wires 672 than with an anchor arm.

Figure 6B:
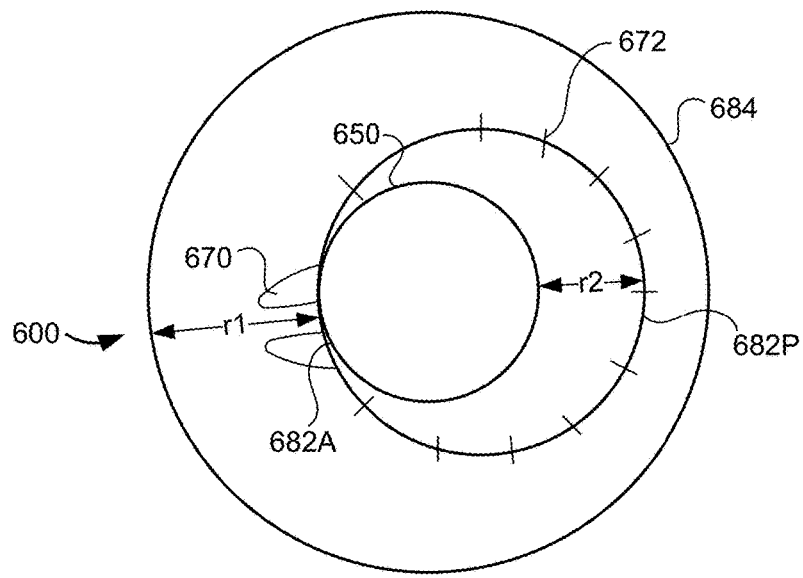
FIG. 6B is a schematic top view of the prosthetic heart valve of FIG. 6A.

FIG. 6B is a top schematic representation of prosthetic heart valve 600. As shown, stent 650 is disposed at the center of prosthetic heart valve 600, while flared portion 684 extends a radial distance r1 away from stent 650 on all sides. In at least some examples, radial distance r1 is between about 50 mm and about 70 mm Posterior body portion 682P extends a radial distance r2 away from stent 650 adjacent the native posterior leaflet, but does not have the same extension at the native anterior leaflet. In at least some examples, radial distance r2 is between about 5 mm and about 25 mm adjacent the posterior leaflet. Additionally, a number of stabilizing wires 672 are circumferentially disposed around body portion 682 with the exception of the region near the left ventricular outflow tract.

Figure 6C:
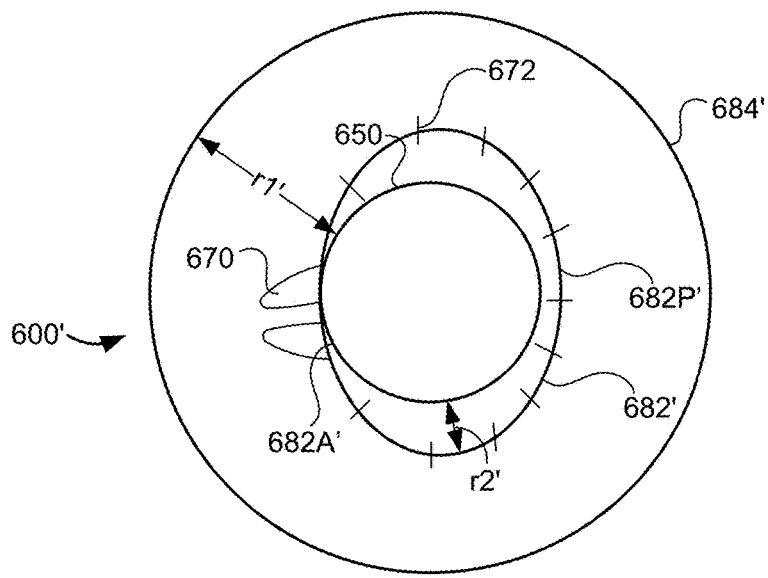
FIG. 6C is a schematic top view of a variant of the prosthetic heart valve of FIG. 6A having an oval flange.
Figure 6D:
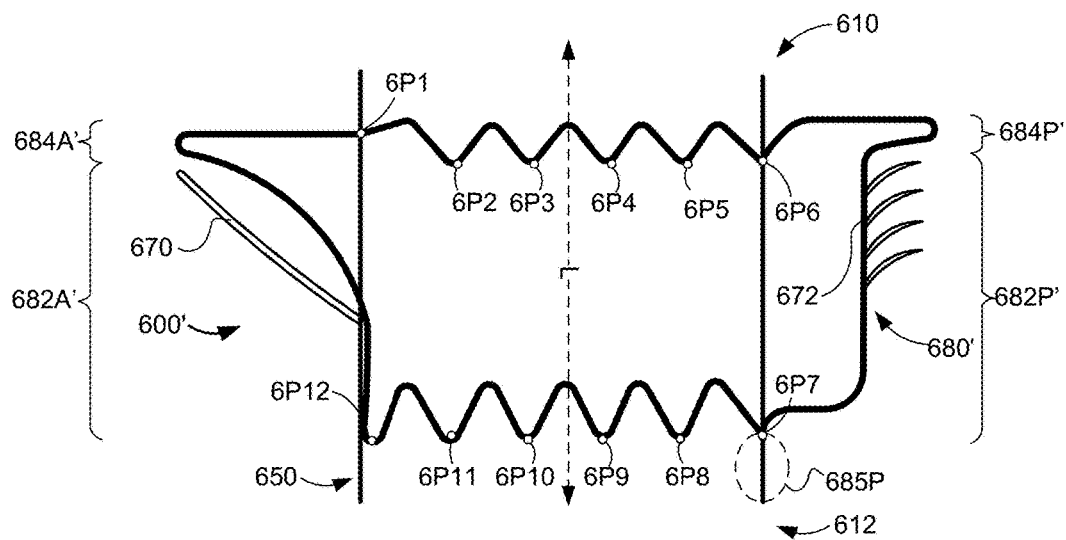
FIG. 6D is a side view of a prosthetic heart valve according to yet another aspect of the disclosure.

A variation of prosthetic heart valve 600 is shown in FIG. 6D and marked as prosthetic heart valve 600'. Prosthetic heart valve 600' includes stent 650 and flange 680' and is similar to prosthetic heart valve 600 with a few exceptions. First, flange 680' includes flared portion 684P' on the posterior side and flared portion 684A' on the anterior side, both of which are flatter than corresponding flared portions 684P,684A and similar to that described with reference to FIG. 5D. Additionally, body portion 682A' is closer to anchoring arms 670 so that a native leaflet or tissue may be grasped therebetween. Attachment point 6P12 is also formed closer to the outflow end 612 so that the device is more uniform along the outflow end.

FIG. 6C is a top schematic representation of prosthetic heart valve 600' which slightly varies from heart valve 600.

As shown, stent 650 is disposed at the center of prosthetic heart valve 600', while flared portion 684' extends a substantially constant radial distance r1' away from stent 650 on all sides. In at least some examples, radial distance r1' is between about 50 mm and about 70 mm. The difference in this configuration is the shape of the body portion 682'. Specifically, body portion 682' has an oval lateral-cross-section instead of being circular, which may be a better fit for certain patients. It is also contemplated the body portion may have a D-shaped lateral-cross-section to match the shape of the native annulus to provide an improved fit. Posterior body portion 682P' extends a radial distance r2' away from stent 650 adjacent the native posterior leaflet, but does not have the same extension at the native anterior leaflet. In at least some examples, radial distance r2' is between about 5 mm and about 25 mm adjacent the posterior leaflet. By combining a flange 680' having portions with an oval, or irregularly-shaped lateral cross-section with a circular stent (and thus, valve assembly) several benefits may be gained. First, circular stents and valve assemblies may be easier to manufacture and their operation is better understood. Thus, it may be easier to maintain this circular configuration of the stent and valve assembly while modifying the outer components (e.g., flange) depending on the intended application. Second, the assembly may be used with large annuli. Specifically, it is postulated that a valve assembly with a 29 mm diameter may provide adequate flow to most patients. Thus, for extremely large annuli, a standard 29 mm valve assembly may be used in conjunction with larger flanges as desired. This reduces the need for making valve assemblies in multiple different sizes, while allowing the prosthetic heart valve to be crimped to the smallest possible diameter. Although it is contemplated that other sized valve assemblies may be used when desired, as valves having smaller diameters reduce crimp profile, while larger valves have the benefit of increasing fluid flow.

Figure 6E:
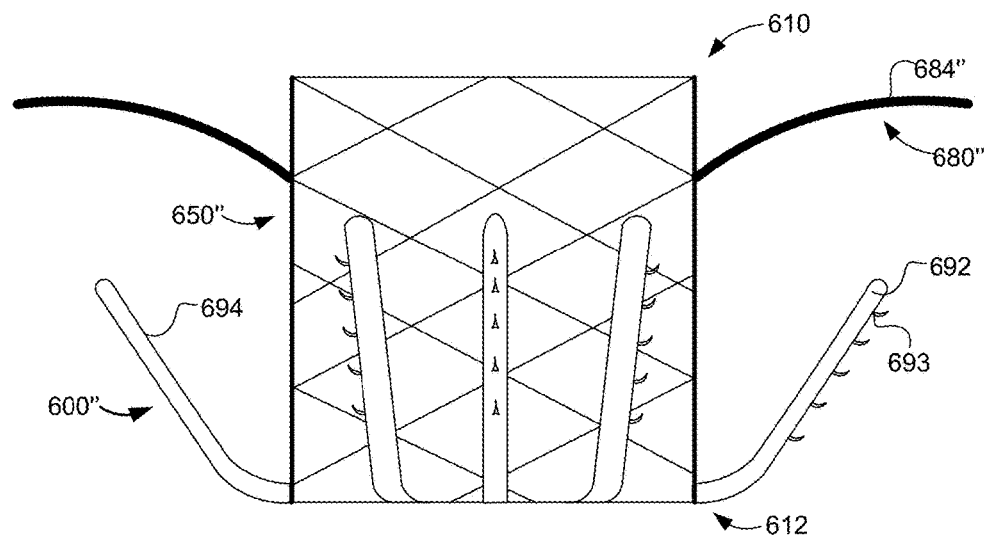
FIG. 6E is a schematic side view of a prosthetic heart valve according to yet another aspect of the disclosure.

Another variation of prosthetic heart valve 600 is shown in FIG. 6E and marked as prosthetic heart valve 600". Prosthetic heart valve 600" includes stent 650" and flange 680" and is similar to prosthetic heart valve 600 with a few exceptions. First, flange 680" is limited only to a flared portion 684" adjacent the atrium and does not include a body portion. Additionally, a number of arms 692 are circumferentially disposed around stent 650" adjacent outflow end 612. Arms 692 may be integrally formed with stent 650" or formed of a separate metallic body that is later welded to the stent. Each of arms 692 includes a number of stabilizing wires 693 similar to those described above, except for arm 694 disposed on the anterior side, which does not include such wires. In one example, anterior arm 694 may be released first to capture a native valve leaflet between it and the rest of stent 650", and arms 692 having wires 693 may be deployed sequentially thereafter. Additionally, arms 692, 694 may be configured to transition between a first, delivery condition and a second, deployed condition, the arms in the first condition extending toward the outflow end and in the second condition extending toward the inflow end.

Figure 7A:
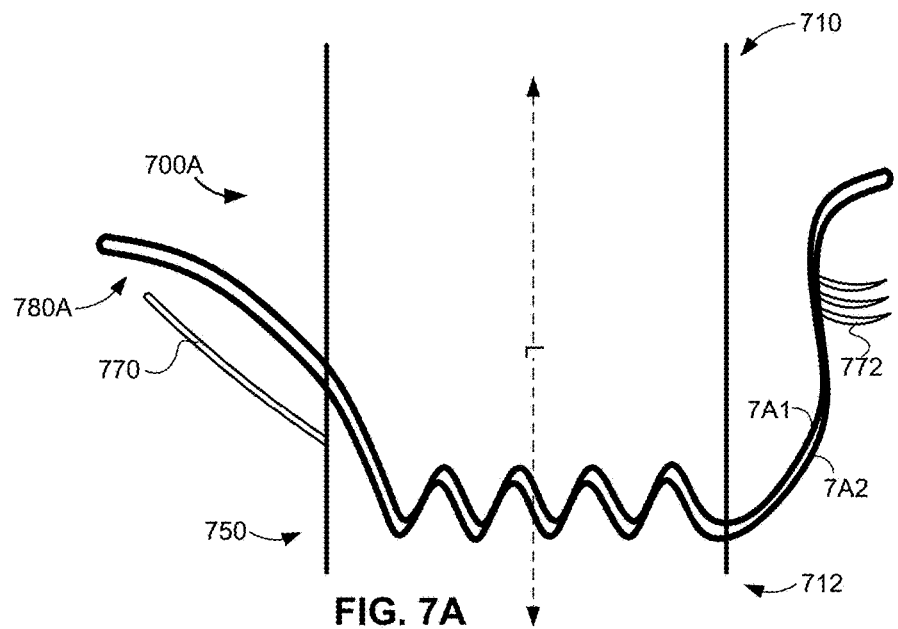
FIG. 7A is a schematic side view of a prosthetic heart valve according to yet another aspect of the disclosure.

FIG. 7A illustrates yet another example of a prosthetic heart valve 700A having stent 750 and asymmetric flange 780A. The flange 780A may be formed of a braided material, such as nitinol, to create various shapes and/or geometries to engage tissue. In this example, flange 780A is formed of two portions, 7A1,7A2 that are joined together. Additionally, flange 780A is disposed closer to outflow end 712 than to inflow end 710. Such a configuration may limit the possibility of obstructing the left ventricular outflow tract. For example, as the anchor arms, flange and atrial seal are brought closer to the outflow side of the stent, it may effectively position the prosthesis closer to the atrium, as opposed to the ventricle, making it less likely to obstruct the outflow tract. Moreover, the use of anchoring arms 770 on one side and stabilizing wires 772 on an opposite side may help in anchoring the prosthetic heart valve as described above. Anchoring arms 770 may also aid in capturing a native valve leaflet and prevent the leaflet from obstructing the left ventricular outflow tract.

Figure 7B:
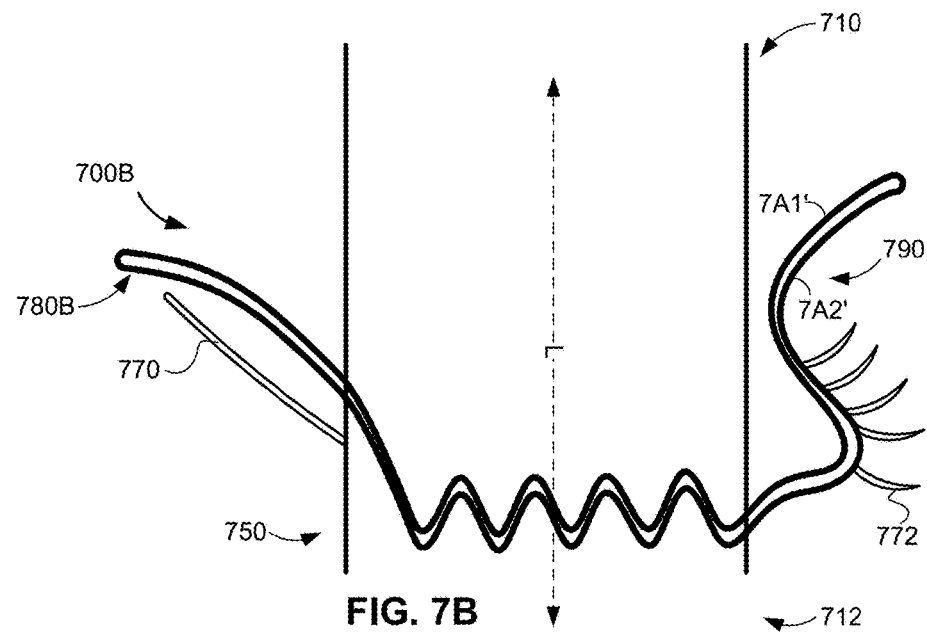
FIG. 7B is a schematic side view of a prosthetic heart valve according to yet another aspect of the disclosure.

FIG. 7B illustrates yet another example of a prosthetic heart valve 700 having stent 750 and asymmetric flange 780B formed of two portions 7A1',7A2'. In this example, flange 780B is substantially similar to flange 780A, except that it also includes an S-shaped curve 790 on the posterior side to sandwich the native valve annulus therein, the S-shaped curve having a number of stabilizing wires 772 disposed on an outer surface thereof. One or more anchoring arms 770 are disposed on an anterior side of the stent opposite S-shaped curve 790.

Figure 7C:
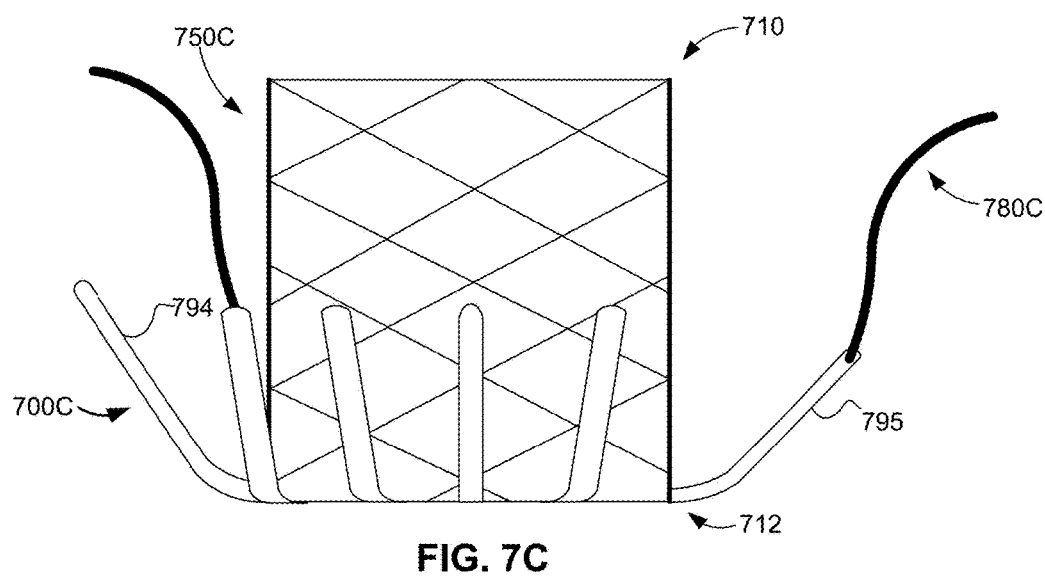
FIG. 7C is a schematic side view of a prosthetic heart valve according to yet another aspect of the disclosure.

In yet another example, prosthetic heart valve 700C having stent 750C and asymmetric flange 780C is shown in FIG. 7C. In this example, flange 780C is formed of a braided material that is substantially similar to flange 780A, but is coupled to base 795, which forms part of stent 750C. Base 795 and flange 780C may be formed of different materials. Specifically, base 795 may be integrally formed with the stent or later welded to the stent, and may be formed of a thicker material that is more fatigue-resistant than just a braid. Alternatively, the entire flange may be made from a laser cut stent so that all of base 795, flange 780C and stent 750C are formed of the same material. A separate arm 794 may be used for sandwiching the native valve leaflet as previously described.

Figure 8:
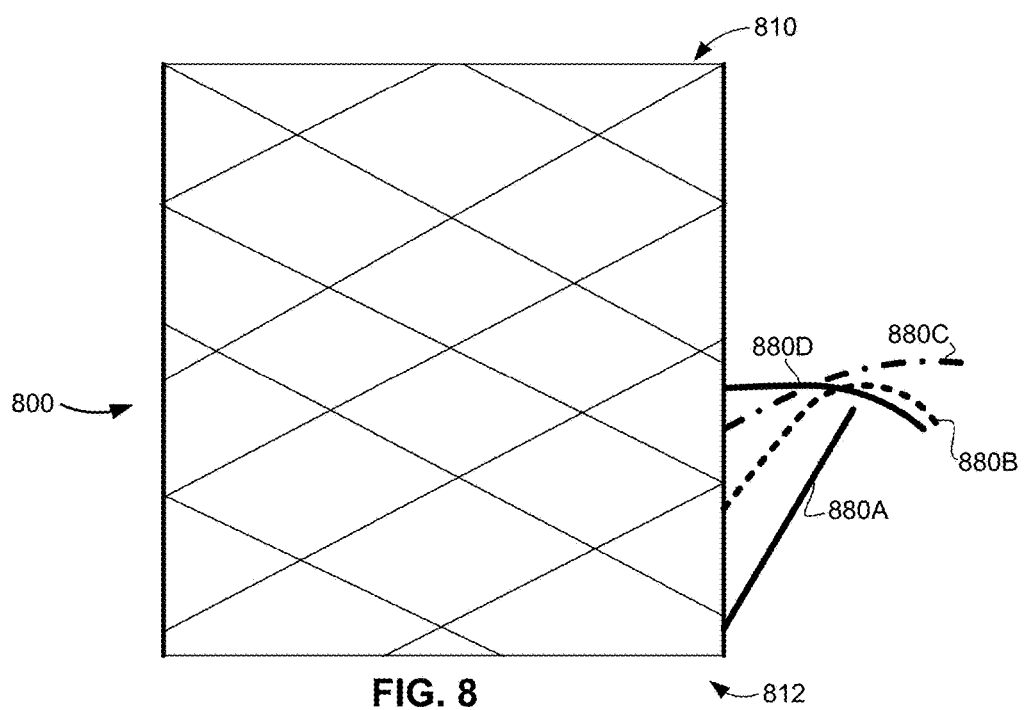
FIG. 8 is a schematic side view showing flanges of different profiles disposed on a stent.

It will be understood that the shape of the flange may be modified as desired. For example, FIG. 8 shows a stent 800 and a number of possible profiles for a flange. Flange 880A is generally straight and extends toward inflow end 810 of the stent 800. Flange 880B likewise initially extends toward inflow end 810, but has a steep curve that allows it to extend back toward outflow end 812. Flange 880C is the flattest of the configurations, and flange 880D has a slight curve and extends toward outflow end 812 as shown. These and other profiles are possible. Additionally, it will be understood that the same or different profiles may be used on the anterior side and the posterior side of the device as previously described. Moreover, as shown, all of the configurations of flanges 880A-D are shown as being attached to the stent closer to outflow end 812 than to inflow end 810. This allows for most of the device to be seated closer to the atrium than the ventricle, reducing the risk of obstruction of the left ventricular outflow tract.

According to the disclosure, a prosthetic heart valve has an inflow end and an outflow end, and may include a stent having a collapsed condition, an expanded condition, and a plurality of cells arranged in circumferential rows, the stent has an anterior side configured and arranged to be disposed adjacent an anterior native valve leaflet, and a posterior side configured and arranged to be disposed adjacent a posterior native valve leaflet, a valve assembly disposed within the stent and with a plurality of leaflets, and a flange disposed about the stent, the flange has a flared portion adjacent the inflow end of the prosthetic heart valve and a body portion that extends from the flared portion to the outflow end, the flange extends between a first set of attachment points adjacent the inflow end, and a second set of attachment points adjacent the outflow end; and/or the flange is formed of a braided mesh, and the body portion extends a first distance toward the outflow end on one side of the prosthetic heart valve, and extends a second distance toward the outflow end on another side of the prosthetic heart valve, the second distance being less than the first distance; and/or the body portion extends over the stent to define a first exposed portion of the stent on the anterior side of the stent, and a second exposed portion of the stent on the posterior side of the stent, the first exposed portion being larger than the second exposed portion; and/or the body portion extends over the stent to define a first exposed portion of the stent on the anterior side of the stent, the first exposed portion being configured and arranged to allow unimpeded blood flow through the left ventricular outflow tract; and/or the body portion covers about half of the stent on an anterior side of the stent; and/or the flared portion is symmetric about a longitudinal axis of the stent; and/or the prosthetic heart valve further includes a cover layer disposed over at least a portion of the flange; and/or the prosthetic heart valve further includes at least one anchor arm disposed adjacent the anterior side of the stent; and/or the prosthetic heart valve further includes a plurality of stabilizing wires disposed adjacent a posterior side of the stent; and/or the flared portion of the flange has a first diameter in an expanded condition of the flange and the body portion of the flange has a second diameter in the expanded condition of the flange, the second diameter being smaller than the first diameter; and/or both the flared portion and the body portion of the flange have circular lateral cross-sections in an expanded condition of the flange;

the flared portion has a circular lateral cross-section in an expanded condition of the flange, and the body portion of the flange has an oval lateral cross-section in an expanded condition of the flange.

According to the disclosure, a prosthetic heart valve may also have an inflow end and an outflow end, a stent having a collapsed condition, an expanded condition, and a plurality of cells arranged in circumferential rows, the stent has an anterior side configured and arranged to be disposed adjacent an anterior native valve leaflet, and a posterior side configured and arranged to be disposed adjacent a posterior native valve leaflet, a valve assembly disposed within the stent and with a plurality of leaflets, and a flange disposed about the stent, the flange being asymmetric about a longitudinal axis such that a posterior side of the flange has a different shape than an anterior side of the flange; and/or the flange is formed of a braided mesh and has a flared portion adjacent the inflow end of the prosthetic heart valve and a body portion extending from the flared portion to the outflow end; and/or the flared portion has a same shape on the anterior side of the flange and on the posterior side of the flange, and the body portion has a different shape on the anterior side of the flange than on the posterior side of the flange; and/or the body portion extends a first distance toward the outflow end on one side of the prosthetic heart valve, and extends a second distance toward the outflow end on another side of the prosthetic heart valve, the second distance being less than the first distance; and/or the body portion extends over the stent to define a first exposed portion of the stent on the anterior side of the stent, and a second exposed portion of the stent on the posterior side of the stent, the first exposed portion being larger than the second exposed portion; and/or the body portion extends over the stent to define a first exposed portion of the stent on the anterior side of the stent, the first exposed portion being configured and arranged to allow unimpeded blood flow through the left ventricular outflow tract; and/or the prosthetic heart valve further includes at least one anchor arm disposed adjacent the anterior side of the stent, and a plurality of stabilizing wires disposed adjacent a posterior side of the stent; and/or the flange is formed of at least two portions of material that overlap one another.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, any of the anchor arms described above may be integrally formed with the stent and laser cut from the stent body. In addition, features of embodiments described herein may be combined with features of other embodiments described herein without departing from the scope of the invention.

The invention claimed is:

1. A prosthetic heart valve having an inflow end and an outflow end, comprising:
   a stent having a collapsed condition, an expanded condition, and a plurality of cells arranged in circumferential rows, the stent having an anterior side configured and arranged to be disposed adjacent an anterior native valve leaflet, and a posterior side configured and arranged to be disposed adjacent a posterior native valve leaflet;
   a valve assembly disposed within the stent and having a plurality of leaflets; and
   a flange disposed about the stent, the flange having a flared portion adjacent the inflow end of the prosthetic heart valve and a body portion extending from the flared portion toward the outflow end,
   wherein the body portion extends a first distance toward the outflow end on one side of prosthetic heart valve and extends a second distance toward the outflow end on another side of the prosthetic heart valve, the second distance being less than the first distance.

2. The prosthetic heart valve of claim 1, wherein the flange is formed of a braided mesh.

3. The prosthetic heart valve of claim 1, wherein the body portion extends over the stent to define a first exposed portion of the stent on the anterior side of the stent, and a second exposed portion of the stent on the posterior side of the stent, the first exposed portion being larger than the second exposed portion.

4. The prosthetic heart valve of claim 3, wherein the first exposed portion is configured and arranged to allow unimpeded blood flow through the left ventricular outflow tract.

5. The prosthetic heart valve of claim 1, wherein the body portion covers about half of the stent on the anterior side of the stent.

6. The prosthetic heart valve of claim 5, wherein the flared portion is symmetric about a longitudinal axis of the stent.

7. The prosthetic heart valve of claim 1, further comprising a covering layer disposed over at least a portion of the flange.

8. The prosthetic heart valve of claim 1, further comprising at least one anchoring arm disposed adjacent the anterior side of the stent.

9. The prosthetic heart valve of claim 1, further comprising a plurality of stabilizing wires disposed adjacent the posterior side of the stent.

10. The prosthetic heart valve of claim 1, wherein the flared portion of the flange has a first diameter in an expanded condition of the flange and the body portion of the flange has a second diameter in the expanded condition of the flange, the second diameter being smaller than the first diameter.

11. The prosthetic heart valve of claim 1, wherein both the flared portion and the body portion of the flange have circular lateral cross-sections in an expanded condition of the flange.

12. The prosthetic heart valve of claim 1, wherein the flared portion has a circular lateral cross-section in an expanded condition of the flange, and the body portion of the flange has an oval lateral cross-section in the expanded condition of the flange.

13. A prosthetic heart valve having an inflow end and an outflow end, comprising:
    a stent having a collapsed condition, an expanded condition, and a plurality of cells arranged in circumferential rows, the stent having an anterior side configured and arranged to be disposed adjacent an anterior native valve leaflet, and a posterior side configured and arranged to be disposed adjacent a posterior native valve leaflet;
    a valve assembly disposed within the stent and having a plurality of leaflets; and
    a flange disposed about the stent, the flange having a flared portion adjacent the inflow end of the prosthetic heart valve and a body portion extending from the flared portion toward the outflow end, the flange being asymmetric about a longitudinal axis such that a posterior side of the flange has a different shape than an anterior side of the flange,
    wherein the flared portion has a same shape on the anterior side of the flange and on the posterior side of the flange, and the body portion has a different shape on the anterior side of the flange than on the posterior side of the flange.

14. The prosthetic heart valve of claim 13, wherein the flange is formed of a braided mesh.

15. The prosthetic heart valve of claim 13, wherein the body portion extends a first distance toward the outflow end on the anterior side of the stent, and extends a second distance toward the outflow end on the posterior side of the stent, the second distance being less than the first distance.

16. The prosthetic heart valve of claim 13, wherein the body portion extends over the stent to define a first exposed portion of the stent on the anterior side of the stent, and a second exposed portion of the stent on the posterior side of the stent, the first exposed portion being larger than the second exposed portion.

17. The prosthetic heart valve of claim 16, wherein the first exposed portion is configured and arranged to allow unimpeded blood flow through the left ventricular outflow tract.

18. The prosthetic heart valve of claim 13, further comprising at least one anchoring arm disposed adjacent the anterior side of the stent, and a plurality of stabilizing wires disposed adjacent the posterior side of the stent.

19. The prosthetic heart valve of claim 13, wherein the flange is formed of at least two portions of material that overlap one another.

* * * * *